United States Patent
Möckel et al.

(10) Patent No.: US 6,670,156 B1
(45) Date of Patent: Dec. 30, 2003

(54) **POLYNUCLEOTIDE ENCODING A DIAMINOPIMELATE EPIMERASE FROM *CORYNEBACTERIUM GLUTAMICUM***

(75) Inventors: Bettina Möckel, Düsseldorf (DE); Walter Pfefferle, Halle (DE); Brigitte Bathe, Salzkotten (DE); Jorn Kalinowski, Bielefeld (DE); Oliver Kirchner, Bielefeld (DE); Michael Hartmann, Bielefeld (DE); Alfred Pühler, Bielefeld (DE)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 09/427,548

(22) Filed: Oct. 27, 1999

(30) Foreign Application Priority Data

Sep. 11, 1999 (DE) .......................... 199 43 587

(51) Int. Cl.[7] .............................. C12P 13/08

(52) U.S. Cl. ................. 435/115; 435/320.1; 435/252.3; 435/254.11; 435/419; 435/325; 536/23.1; 536/23.2

(58) Field of Search ............. 536/23.1, 23.2; 435/320.1, 252.32, 115, 252.3

(56) References Cited

U.S. PATENT DOCUMENTS

| | | | |
|---|---|---|---|
| 4,560,654 A | | 12/1985 | Miwa et al. |
| 4,954,441 A | | 9/1990 | Katsumata et al. |
| 6,040,160 A | * | 3/2000 | Kojima et al. |
| 2003/0049804 A1 | | 3/2003 | Pompejus et al. |

FOREIGN PATENT DOCUMENTS

| | | | |
|---|---|---|---|
| EP | 0 854 189 | | 7/1998 |
| EP | 1 108 790 | | 6/2001 |
| WO | WO00/56858 | * | 9/2000 |
| WO | 2000056858 A2 | * | 9/2000 |
| WO | WO 01/00843 | | 1/2001 |
| WO | 2001000843 A2 | * | 1/2001 |

OTHER PUBLICATIONS

Richaud et al. Molecular cloning, characterization, and chromosomal localization of dapF, the *Escherichia coli* gene for diaminopimeliate epimerase. J. Bacteriol. (1987) 169(4):1454–1459.*

Cole et al. GenBank Accession No. Z98209 (Jun. 1998).*

Sahm et al. Metabolic design in amino acid producing bacterium *Corynebacterium glutamicum*. FEMS Microbiology Reviews (1995) 16:243–252.*

Pompejus et al. GenBank Accession No. AXO63719 (Jan. 24, 2001).*

Pompejus et al. GenBank Accession No. CAC25100 (Jan. 24, 2001).*

Malumbres et al., "Molecular Control Mechanisms of Lysine and Threonine Biosynthesis in Amino Acid–Producing Corynebacteria: Redirecting Carbon Flow," *FEMS Microbiology Letters*, 1996, pp. 103–114.

Wehrmann et al., "Different Modes of Diaminopimelate Synthesis and Their Role in Cell Wall Integrity: a Study with *Corynebacterium glutamicum*," *Journal of Bacteriology*, Jun. 1998, pp. 3159–3165.

Griffais, "Primer Used to Amplify Chlamydia Pneumoniae Polynucleotides," *Database EMBL Online*, Jun. 1999.

Richaud et al., Nucleotide Sequence of the dapF Gene and Flanking Regions from *Escherichia coli* K12, *Nucleic Acids Research*, vol. 16, No. 21, 1988.

(List continued on next page.)

*Primary Examiner*—Ponnathapu Achutamurthy
*Assistant Examiner*—Kathleen Kerr
(74) *Attorney, Agent, or Firm*—Pillsbury Winthrop LLP

(57) ABSTRACT

The present application is directed to a diaminopimelate epimerase from *Corynebacterium glutamicum* and to polynucleotides encoding this enzyme. The gene has been given the designation "dapF."

12 Claims, 2 Drawing Sheets

OTHER PUBLICATIONS

Sahm et al., "Construction of L–lysine, L–threonine–, or L–isoleucine–overproducing strains of *Corynebacterium glutamicum*", Annals of the New York Academy of Science, vol. 782, p. 25–39 (1996).

Gilvarg, "The enzymatic synthesis of diaminopimelic acid", (1958), The Journal of Biological Chemistry, vol. 233: p. 1501–1504.

Weinberger & Gilvarg, "Bacterial distribution of the use of succinyl and acetyl blocking groups in diaminopimelic acid biosynthesis", (1970), Journal of Bacteriology, vol. 101, p. 323–324.

Misono et al., Meso–$\alpha,\epsilon$–diaminopimelate dD–dehydrogenase: distribution and the reaction product:, (1976) Journal of Bacteriology, vol. 137, p. 22–27.

Schrumpf et al., "A functionally split pathway for lysine synthesis in *Corynebacterium glutamicum*", Journal of Bacteriology, vol. 173, p. 4510–4516 (1991).

Marx et al., "Response of the central metabolism of *Corynebacterium glutamicum* to different flux burdens", Biotechnology and Bioengineering, vol. 56, p. 168–180 (1997).

Sonntag, "Flux partitioning in the split pathway of lysine synthesis in *Corynebacterium glutamicum* . Quantification by $^{13}$C– and $^{1}$H–NMR spectroscopy", European Journal of Biochemistry, vol. 213, p. 1325–1331 (1993).

Wehrmannn et al., "Fuctional analysis of sequences adjacent to dapE of *Corynebacterium glutamicum* reveals the presence of aroP, which encodes the aromatic amino acid transporter", Journal of Bacteriology, vol. 177, p. 5991–5993 (1995).

Wehrmannn et al., "Different modes of diaminopimelate synthesis and their role in cell wall integrity: a study with *Corynebacterium glutamicum*", Journal of Bacteriology, vol. 180, p. 3159–3165 (1998).

\* cited by examiner

SEQUENCE LISTING

```
<160> NUMBER OF SEQ ID NOS: 4

<210> SEQ ID NO 1
<211> LENGTH: 1084
<212> TYPE: DNA
<213> ORGANISM: Corynebacterium glutamicum
<220> FEATURE:
<221> NAME/KEY: -35_signal
<222> LOCATION: (117)..(123)
<220> FEATURE:
<221> NAME/KEY: -10_signal
<222> LOCATION: (138)..(143)
<220> FEATURE:
<221> NAME/KEY: CDS
<222> LOCATION: (151)..(981)

<400> SEQUENCE: 1
agacgccttc gaacgcacgg tcaccggaac cagacgctat gtcaggcgcc aacgcagctg      60
gttcaacaga gaccaccgcg tgtcctgggt cgacgcctct ggcgatccca ccgcacaagc     120
cttggagatt ttgggtctac aatagcgagg gtg aat ttg acc atc ccc ttt gcc     174
                                 Met Asn Leu Thr Ile Pro Phe Ala
                                   1               5 aaa ggc cac gcc acc gaa aac gac ttc atc atc atc ccc gat gag gat     222
Lys Gly His Ala Thr Glu Asn Asp Phe Ile Ile Ile Pro Asp Glu Asp
         10                  15                  20 gcg cgc cta gat tta act cca gaa atg gtg gtc acg ctg tgt gac cgc     270
Ala Arg Leu Asp Leu Thr Pro Glu Met Val Val Thr Leu Cys Asp Arg
```

-continued

```
          25                  30                  35                  40
cgc gcc ggg atc ggt gct gat ggt atc ctc cgc gtg gtt aaa gct gca                318
Arg Ala Gly Ile Gly Ala Asp Gly Ile Leu Arg Val Val Lys Ala Ala
                45                  50                  55 gac gta gaa ggc tcc acg gtc gac cca tcg ctg tgg ttc atg gat tac                366
Asp Val Glu Gly Ser Thr Val Asp Pro Ser Leu Trp Phe Met Asp Tyr
            60                  65                  70 cgc aac gcc gat gga tct ttg gct gaa atg tgc ggc aat ggt gtg cgc                414
Arg Asn Ala Asp Gly Ser Leu Ala Glu Met Cys Gly Asn Gly Val Arg
        75                  80                  85 ctg ttc gcg cac tgg ctg tac tcc cgc ggt ctt gtt gat aat acg agc                462
Leu Phe Ala His Trp Leu Tyr Ser Arg Gly Leu Val Asp Asn Thr Ser
    90                  95                 100 ttt gat atc ggt acc cgc gcc ggt gtc cgc cac gtt gat att ttg cag                510
Phe Asp Ile Gly Thr Arg Ala Gly Val Arg His Val Asp Ile Leu Gln
105                 110                 115                 120 gca gat caa cat tct gcg cag gtc cgc gtt gat atg ggc atc cct gac                558
Ala Asp Gln His Ser Ala Gln Val Arg Val Asp Met Gly Ile Pro Asp
                125                 130                 135 gtc acg gga tta tcc acc tgc gac atc aac ggc caa gta ttc gct ggc                606
Val Thr Gly Leu Ser Thr Cys Asp Ile Asn Gly Gln Val Phe Ala Gly
            140                 145                 150 ctt ggc gtt gat atg ggt aac cca cac cta gcg tgc gtt gtg ccg ggc                654
Leu Gly Val Asp Met Gly Asn Pro His Leu Ala Cys Val Val Pro Gly
        155                 160                 165 tta agt gcg tcg gct ctt gcc gat atg gaa ctg cgc gca cct acg ttt                702
Leu Ser Ala Ser Ala Leu Ala Asp Met Glu Leu Arg Ala Pro Thr Phe
    170                 175                 180 gat cag gaa ttc ttc ccc cac ggt gtg aac gta gaa atc gtc aca gaa                750
Asp Gln Glu Phe Phe Pro His Gly Val Asn Val Glu Ile Val Thr Glu
185                 190                 195                 200 tta gaa gat gac gca gta tcg atg cgc gtg tgg gaa cgc gga gtg ggc                798
Leu Glu Asp Asp Ala Val Ser Met Arg Val Trp Glu Arg Gly Val Gly
                205                 210                 215 gaa acc cgc tcc tgt ggc acg gga acc gtt gct gca gcg tgt gct gct                846
Glu Thr Arg Ser Cys Gly Thr Gly Thr Val Ala Ala Ala Cys Ala Ala
            220                 225                 230 tta gct gat gct gga ttg gga gaa ggc aca gtt aaa gtg tgc gtt cca                894
Leu Ala Asp Ala Gly Leu Gly Glu Gly Thr Val Lys Val Cys Val Pro
        235                 240                 245 ggt ggg gaa gta gaa gtc cag atc ttt gac gac ggc tcc aca ctc acc                942
Gly Gly Glu Val Glu Val Gln Ile Phe Asp Asp Gly Ser Thr Leu Thr
    250                 255                 260 ggc cca agc gcc atc atc gca ctc ggt gag gtg cag atc                            991
Gly Pro Ser Ala Ile Ile Ala Leu Gly Glu Val Gln Ile      taagattcgc
265                 270                 275 gattgtagtt cggcccaagt ttctgggccg ctttacgcgc atccagccac gtttcccgca            1051
gctctagtgc gcgctcgtcc gttactttga gaa                                         1084

<210> SEQ ID NO 2
<211> LENGTH: 277
<212> TYPE: PRT
<213> ORGANISM: Corynebacterium glutamicum

<400> SEQUENCE: 2

Met Asn Leu Thr Ile Pro Phe Ala Lys Gly His Ala Thr Glu Asn Asp
 1               5                  10                  15

Phe Ile Ile Ile Pro Asp Glu Asp Ala Arg Leu Asp Leu Thr Pro Glu
            20                  25                  30
```

-continued

```
Met Val Val Thr Leu Cys Asp Arg Arg Ala Gly Ile Gly Ala Asp Gly
            35                  40                  45

Ile Leu Arg Val Val Lys Ala Ala Asp Val Glu Gly Ser Thr Val Asp
    50                  55                  60

Pro Ser Leu Trp Phe Met Asp Tyr Arg Asn Ala Asp Gly Ser Leu Ala
65                  70                  75                  80

Glu Met Cys Gly Asn Gly Val Arg Leu Phe Ala His Trp Leu Tyr Ser
                85                  90                  95

Arg Gly Leu Val Asp Asn Thr Ser Phe Asp Ile Gly Thr Arg Ala Gly
            100                 105                 110

Val Arg His Val Asp Ile Leu Gln Ala Asp Gln His Ser Ala Gln Val
            115                 120                 125

Arg Val Asp Met Gly Ile Pro Asp Val Thr Gly Leu Ser Thr Cys Asp
130                 135                 140

Ile Asn Gly Gln Val Phe Ala Gly Leu Gly Val Asp Met Gly Asn Pro
145                 150                 155                 160

His Leu Ala Cys Val Val Pro Gly Leu Ser Ala Ser Ala Leu Ala Asp
                165                 170                 175

Met Glu Leu Arg Ala Pro Thr Phe Asp Gln Glu Phe Phe Pro His Gly
            180                 185                 190

Val Asn Val Glu Ile Val Thr Glu Leu Glu Asp Asp Ala Val Ser Met
            195                 200                 205

Arg Val Trp Glu Arg Gly Val Gly Glu Thr Arg Ser Cys Gly Thr Gly
            210                 215                 220

Thr Val Ala Ala Ala Cys Ala Ala Leu Ala Asp Ala Gly Leu Gly Glu
225                 230                 235                 240

Gly Thr Val Lys Val Cys Val Pro Gly Gly Glu Val Glu Val Gln Ile
                245                 250                 255

Phe Asp Asp Gly Ser Thr Leu Thr Gly Pro Ser Ala Ile Ile Ala Leu
            260                 265                 270

Gly Glu Val Gln Ile
        275

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 3
atcgtcaatt gcaccgcaca agccttggag a                              31

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 4
gacgatggat cctaacggac gagcgcgcac ta                             32
```

POLYNUCLEOTIDE ENCODING A DIAMINOPIMELATE EPIMERASE FROM *CORYNEBACTERIUM GLUTAMICUM*

BACKGROUND OF THE INVENTION

1. Field of the Invention

The invention provides nucleotide sequences which code for the dapF gene and a process for the fermentative preparation of L-lysine using coryneform bacteria in which the dapF gene is amplified.

2. Background Invention

L-Lysine is used in human medicine and in the pharmaceuticals industry, but in particular in animal nutrition.

It is known that L-lysine is prepared by fermentation of strains of coryneform bacteria, in particular *Corynebacterium glutamicum*. Because of its great importance, work is constantly being undertaken to improve the preparation process. Improvements to the process can relate to fermentation measures, such as for example stirring and supply of oxygen, or the composition of the nutrient media, such as for example the sugar concentration during the fermentation, or the working up to the product form by for example ion exchange chromatography, or the intrinsic output properties of the microorganism itself.

Methods of mutagenesis, selection and mutant selection are used to improve the output properties of these microorganisms. Strains which are resistant to antimetabolites, such for example the lysine analogue S-(2-aminoethyl)-cysteine, or are auxotrophic for amino acids of regulatory importance and produce L-lysine are obtained in this manner.

Methods using recombinant DNA techniques have also been employed for some years for improving Corynebacterium strains which produce L-lysine, by amplifying individual lysine biosynthesis genes and investigating the effect on the L-lysine production. Review articles in this context are to be found, inter alia, in Kinoshita ("Glutamic Acid Bacteria", in: Biology of Industrial Microorganisms, Demain and Solomon (Eds.), Benjamin Cummings, London, UK, 1985, 115–142), Hilliger (BioTec 2, 40–44 (1991)), Eggeling (Amino Acids 6:261–272 (1994)), Jetten and Sinskey (Critical Reviews in Biotechnology 15, 73–103 (1995)) and Sahm et al. (Annuals of the New York Academy of Science 782, 25–39 (1996)).

In prokaryotes, three different routes are known for the biosynthesis of D,L-diaminopimelate- or L-lysine. These routes differ in the reaction of L-piperidine-2,6-dicarboxylate (tetrahydrodipicolinate).

In the succinylase route, tetrahydrodipicolinate is converted into D,L diaminopimelate via a succinylation by tetrahydrodipicolinate succinylase, subsequent transamination (N-succinyl-amino-ketopimelate transaminase) of the keto group, desuccinylation (N-succinyl-amino-ketopimelate desuccinylase) and then epimerization (diaminopimelate epimerase) (Gilvarg, 1958, The Journal of Biological Chemistry, 233: 1501–1504).

In the acetylase route, which is present in Bacillus subtilis and Bacillus megaterium, the acylation of tetrahydrodipicolinate is carried out by an acetyl radical (Weinberger & Gilvarg, 1970, Journal of Bacteriology, 101:323–324).

A third biosynthesis route is described for B. sphaericus (Misono et al., 1976, Journal of Bacteriology, 137:22–27). In this biosynthesis step, which is called the dehydrogenase route, direct reductive amination of the tetrahydrodipicolinate to D,L-DAP takes place.

With the aid of genetic and enzymatic studies, Schrumpf et al. (Journal of Bacteriology 173, 4510–4516 (1991)) showed that in *Corynebacterium glutamicum*, lysine biosynthesis takes place both by the dehydrogenase route and by the succinylase route.

In vivo NMR studies by Marx et al., (Biotechnology and Bioengineering 56, 168–180 (1997)) and Sonntag (European Journal of Biochemistry 213: 1325–1331 (1993)) have shown that in *Corynebacterium glutamicum* both the succinylase route and the dehydrogenase route contribute towards the production of L-lysine.

The gene for desuccinylase (dapE) from *Corynebacterium glutamicum* has been cloned and sequenced by Wehrmannn et al. (Journal of Bacteriology 177: 5991–5993 (1995)). It has also be possible to clone and sequence the gene for succinylase (dapD) from *Corynebacterium glutamicum* (Wehrmannn et al,. Journal of Bacteriology 180, 3159–3165 (1998)).

SUMMARY OF THE INVENTION

OBJECT OF THE INVENTION

The inventors had the object of providing new measures for improved fermentative preparation of L-lysine.

DESCRIPTION OF THE INVENTION

L-Lysine is used in human medicine, in the pharmaceuticals industry and in particular in animal nutrition. There is therefore a general interest in providing new improved processes for the preparation of L-lysine.

When L-lysine or lysine are mentioned in the following, not only the base but also the salts, such as for example lysine monohydrochloride or lysine sulfate, are also meant.

The invention provides an isolated polynucleotide from coryneform bacteria, comprising a polynucleotide sequence chosen from the group consisting of a) polynucleotide which is identical to the extent of at least 70% to a polynucleotide which codes for a polypeptide which comprises the amino acid sequence of SEQ ID No. 2, b) polynucleotide which is identical to the extent of at least 70% to a polynucleotide which codes for the polypeptide which is expressed by the dapF gene contained on plasmid pEC-XT99A-dapF in the deposited *C. glutamicum* strain DSM 12968, c) polynucleotide which codes for a polypeptide which comprises an amino acid sequence which is identical to the extent of at least 70% to the amino acid sequence of SEQ ID No. 2, d) polynucleotide which is complementary to the polynucleotides of a), b) or c), and e) polynucleotide comprising at least 15 successive bases of the polynucleotide sequence of a), b), c) or d).

The invention also provides a polynucleotide preferably being a DNA which is capable of replication, comprising:

(i) the nucleotide sequence shown in SEQ ID no. 1, or (ii) at least one sequence which corresponds to sequence (i) within the range of the degeneration of the genetic code, or (iii) at least one sequence which hybridizes with the sequence complementary to sequence (i) or (ii), and optionally (iv) sense mutations of neutral function in (i).

The invention also provides
a polynucleotide that is capable of replication in coryneform bacteria, which is preferably recombinant DNA, comprising the nucleotide sequence as shown in SEQ ID no. 1,
a polynucleotide that is capable of replication in coryneform bacteria, which is preferably recombinant DNA, which codes for a polypeptide which comprises the amino acid sequence as shown in SEQ ID No.2,
a vector containing the polynucleotide sequence as described in (i)–(iv) above, in particular pEC-XT99A-dapF, deposited as DSM 12968.
and coryneform bacteria serving as the host cell, which contain the vector a shuttle vector pEC-XT99A-dapF characterized at the restriction map shown in FIG. 2, which has been deposited under the designation DSM 12968.

The invention also provides polynucleotides which substantially comprise a polynucleotide sequence, which are obtainable by screening by means of hybridization of a corresponding gene library, which comprise the complete gene with the polynucleotide sequence corresponding to SEQ ID no. 1, with a probe which comprises the sequence of the polynucleotide mentioned, according to SEQ ID no. 1 or a fragment thereof, and isolation of the DNA sequence mentioned.

Polynucleotide sequences according to the invention are suitable as hybridization probes for RNA, CDNA and DNA, in order to isolate, full length cDNA which encodes diamindpimelate epimerase and to isolate those cDNA or genes which have a high similarity of sequence with that of the diaminopimelate epimerase gene.

Polynucleotide sequences according to the invention are furthermore suitable as primers for the preparation of DNA of genes which code for diaminopimelate epimerase by the polymerase chain reaction (PCR).

Such oligonucleotides which serve as probes or primers comprise at least 30, preferably at least 20, especially preferably at least 15 successive bases. Oligonucleotides which have a length of at least 40 or 50 base pairs are also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

"Polypeptides" is understood as meaning peptides or proteins which comprise two or more amino acids bonded via peptide bonds.

The polypeptides according to the invention include a polypeptide according to SEQ ID No. 2, in particular those with the biological activity of diaminopimelate epimerase, and also those which are identical to the extent of at least 70% to the polypeptide according to SEQ ID No. 2, and preferably are identical to the extent of 80% and in particular to the extent of 90% to 95% to the polypeptide according to SEQ ID no. 2, and have the activity mentioned.

The invention also provides a process for the fermentative preparation of L-lysine using coryneform bacteria which in particular already produce L-lysine, and in which the nucleotide sequences which code for the dapF gene are amplified, in particular over-expressed.

The term "amplification" in this connection describes the increase in the intracellular activity of one or more enzymes in a microorganism which are coded by the corresponding DNA, for example by increasing the number of copies of the gene or genes, using a potent promoter or using a gene which codes for a corresponding enzyme having a high activity, and optionally combining these measures.

The microorganisms which the present invention provides can prepare L-lysine from glucose, sucrose, lactose, fructose, maltose, molasses, starch, cellulose or from glycerol and ethanol. They can be representatives of coryneform bacteria, in particular of the genus Corynebacterium. Of the genus Corynebacterium, there may be mentioned in particular the species *Corynebacterium glutamicum*, which is known among specialists for its ability to produce L-amino acids.

Suitable strains of the genus Corynebacterium, in particular of the species *Corynebacterium glutamicum*, are, for example, the known wild-type strains

*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020 and L-lysine-producing mutants or strains produced therefrom, such as, for example

*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463 and (sic)
*Corynebacterium glutamicum* FERM-P 6464
*Corynebacterium glutamicum* DSM5715

The inventors have succeeded in isolating the new dapF gene of *C. glutamicum* which codes for the enzyme diaminopimelate epimerase (EC 5.1.1.7).

To isolate the dapF gene or also other genes of *C. glutamicum*, a gene library of this microorganism is first set up in *E. coli*. The setting up of gene libraries is described in generally known textbooks and handbooks. The textbook by Winnacker: Gene und Klone, Eine Einführung in die Gentechnologie (Verlag Chemie, Weinheim, Germany, 1990) or the handbook by Sambrook et al.: Molecular Cloning, A Laboratory Manual (Cold Spring Harbor Laboratory Press, 1989) may be mentioned as an example. A well-known gene library is that of the *E. coli* K-12 strain W3110 set up in λ vectors by Kohara et al. (Cell 50, 495–508 (1987)). Bathe et al. (Molecular and General Genetics, 252:255–265, 1996) describe a gene library of *C. glutamicum* ATCC13032, which was set up with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575). Börmann et al. (Molecular Microbiology 6(3), 317–326)) in turn describe a gene library of *C. glutamicum* ATCC13032 using the cosmid pHC79 (Hohn and Collins, Gene 11, 291–298 (1980)). To prepare a gene library of *C. glutamicum* in *E. coli* it is also possible to use plasmids such as pBR322 (Bolivar, Life Sciences, 25, 807–818 (1979)) or pUC9 (Viera et al., 1982, Gene, 19:259–268). Suitable hosts are, in particular, those *E. coli* strains which are restriction- and recombination-defective. An example of these is the strain DH5αmcr, which has been described by Grant et al. (Proceedings of the National Academy of Sciences USA, 87 (1990) 4645–4649). The long DNA fragments cloned with the aid of cosmids can then in turn be subcloned and subsequently sequenced in the usual vectors which are suitable for sequencing, such as is described for example by Sanger et al. (Proceedings of the National Academy of Sciences of the United States of America, 74:5463–5467, 1977).

The new DNA sequence of *C. glutamicum* which codes for the dapF gene and which is a constituent of the present invention as SEQ ID NO 1 was obtained in this manner. The amino acid sequence of the corresponding protein has furthermore been derived from the present DNA sequence by the methods described above. The resulting amino acid sequence of the dapF gene product is shown in SEQ ID NO 2.

Coding DNA sequences which result from SEQ ID NO 1 by the degeneracy of the genetic code are also a constituent of the invention. In the same way, DNA sequences which hybridize with SEQ ID NO 1 or parts of SEQ ID NO 1 are a constituent of the invention. Conservative amino acid exchanges, such as for example exchange of glycine for alanine or of aspartic acid for glutamic acid in proteins, are furthermore known among experts as "sense mutations" which do not lead to a fundamental change in the activity of the protein, i.e. are of neutral function. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences which result in a corresponding manner from SEQ ID NO 2 are also a constituent of the invention.

In the same way, DNA sequences which hybridize with SEQ ID NO 1 or parts of SEQ ID NO 1 are a constituent of the invention. Finally, DNA sequences which are prepared by the polymerase chain reaction (PCR) using primers which result from SEQ ID NO 1 are a constituent of the invention. Such oligonucleotides typically have a length of at least 15 base pairs.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) and in Liebl et al. (International Journal of Systematic Bacteriology (1991) 41:255–260). Instructions for amplification of DNA sequences with the aid of the polymerase chain reaction (PCR) can be found by the expert, inter alia, in the handbook by Gait: Oligonukleotide [sic] synthesis: a practical approach (IRL Press, Oxford, UK, 1984) and in Newton and Graham: PCR (Spektrum Akademischer Verlag, Heidelberg, Germany, 1994).

The inventors have found that coryneform bacteria produce L-lysine in an improved manner after over-expression of the dapF gene.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative L-lysine production. The expression is likewise improved by measures to prolong the life of the m-RNA. Furthermore, the enzyme activity is also increased by preventing the degradation of the enzyme protein. The genes or gene constructions can either be present in plasmids with a varying number of copies, or can be integrated and amplified in the chromosome. Alternatively, an over-expression of the genes in question can furthermore be achieved by changing the composition of the media and the culture procedure.

Instructions in this context can be found by the expert, inter alia, in Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in European Patent Specification EPS 0 472 869, in U.S. Pat. No. 4,601,893, in Schwarzer and Pühler (Bio/Technology 9, 84–87 (1991)), in Reinscheid et al. (Applied and Environmental Microbiology 60, 126–132 (1994)), in LaBarre et al. (Journal of Bacteriology 175, 1001–1007 (1993)), in Patent Application WO 96/15246, in Malumbres et al. (Gene 134, 15–24 (1993)), in Japanese Laid-Open Specification JP-A-10-229891, in Jensen and Hammer (Biotechnology and Bioengineering 58, 191–195 (1998)), in Makrides (Microbiological Reviews 60:512–538 (1996)) and in known textbooks of genetics and molecular biology.

An example of a plasmid with the aid of which the dapF gene can be over-expressed is pEC-XT99A-dapF (FIG. 2), which is contained in the strain DSM5715/pEC-XT99A-dapF. Plasmid pEC-XT99A-dapF is an *E. coli-C. glutamicum* shuttle vector based on the plasmid pEC-XT99A (FIG. 1). This plasmid vector contains the replication region of the plasmid pGA1 (U.S. Pat. No. 5,175,108) and the tetracycline resistance gene of the plasmid pAG1 (Accession No. AF121000 of the National Center for Biotechnology Information, Bethesda, Md., USA). Other plasmid vectors which are capable of replication in *C. glutamicum*, such as e.g. pEKEx1 (Eikmanns et al., Gene 102:93–98 (1991)) or pZ8-1 (EP-B 0 375 889) can be used in the same way.

In addition, it may be advantageous for the production of L-lysine to over-express one or more enzymes of the lysine biosynthesis route, in addition to the dapF gene. Thus, for example at the same time the dapA gene which codes for dihydrodipicolinate synthase can be over-expressed (EP-B 0 197 335), or at the same time a DNA fragment which imparts S-(2-aminoethyl)-cysteine resistance can be amplified (EP-A 0 088 166), or at the same time the dapD gene which codes for tetradihydrodipicolinate succinylase (Wehrmann et al., Journal of Bacteriology 180, 3159–3165 (1998)), or at the same time the dapE gene which codes for succinyldiaminopimelate desuccinylase (Wehrmann et al., Journal of Bacteriology 177:5991–5993 (1995)) can be over-expressed.

In addition to over-expression of the dapF gene it may furthermore be advantageous, for the production of L-lysine, to eliminate undesirable side reactions (Nakayama: "Breeding of Amino Acid Producing Micro-organisms", in: Overproduction of Microbial Products, Krumphanzl, Sikyta, Vanek (eds.), Academic Press, London, UK, 1982).

The microorganisms prepared according to the invention can be cultured continuously or discontinuously in the batch process (batch culture) or in the fed batch (feed process) or repeated fed batch process (repetitive feed process) for the purpose of production of L-lysine. A summary of known culture methods is described in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981). Sugars and carbohydrates, such as for example glucose, sucrose, lactose, fructose, maltose, molasses, starch and cellulose, oils and fats, such as for example soya oil, sunflower oil, groundnut oil and coconut fat, fatty acids, such as for example palmitic acid, stearic acid and linoleic acid, alcohols, such as for example glycerol and ethanol, and organic acids, such as for example acetic acid, can be used as the source of carbon. These substances can be used individually or as a mixture. Organic nitrogen-containing compounds, such as peptones, yeast extract, meat extract, malt extract, corn steep liquor, soya bean flour and urea, or inorganic compounds, such as ammonium sulphate, ammonium chloride, ammonium phosphate, ammonium carbonate and ammonium nitrate, can be used as the source of nitrogen. The sources of nitrogen can be used individually or as a mixture. Phosphoric acid, potassium dihydrogen phosphate or dipotassium hydrogen phosphate or the corresponding sodium-containing salts can be used as the source of phosphorus. The culture medium must furthermore comprise salts of metals, such as for example magnesium sulfate or iron sulfate, which are necessary for growth. Finally, essential growth substances, such as amino acids and vitamins, can be employed in addition to the abovementioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH. Antifoams, such as for example fatty acid polyglycol esters, can be employed to control the development of foam. Suitable substances having a selective action, for example antilbiotics, can be added to the medium to maintain the stability of plasmids. To maintain aerobic conditions, oxygen or oxygen-containing gas mixtures, such as for example air, are introduced into the culture. The temperature of the culture is usually 20° C. to 45° C., and preferably 25° C. to 40° C. Culturing is continued until a maximum of lysine has formed. This target is usually reached within 10 hours to 160 hours.

The analysis of L-lysine can be carried out by anion exchange chromatography with subsequent ninhydrin derivatization, as described by Spackman et al. (Analytical Chemistry, 30, (1958), 1190).

The following microorganisms have been deposited at the Deutsche Sammlung Fur Mikrorganismen und Zellkuturen (DSMZ=German Collection of Microorganisms and Cell Cultures, Mascheroder Web 1b, 38124 Braunschweig, Germany) in accordance with the Budapest Treaty: *Corynebacterium glutamicum* strain DSM5715/pEC-XT99A as DSM 12967; and *Corynebacterium glutamicum* strain DSM5715/pEC-XT99A-dapF as DSM 12968.

In particular, the deposit labeled accession number DSM 12968 refers to a sample of *Corynebacterium glutamicum*, containing plasmid pEC-XT99A-dapF, deposited under the Budapest Treaty on the International Recognition of the Deposit of Microorganisms for the Purposes of Patent Procedure. The deposit was made on Aug. 5, 1999 at the aforementioned international depository.

The process according to the invention is used for fermentative preparation of L-lysine.

DETAILED DESCRIPTION OF THE INVENTION

EXAMPLES

The present invention is explained in more detail in the following with the aid of embodiment examples.

Example 1

Preparation of a genomic cosmid gene library from *Corynebacterium glutamicum* ATCC 13032

Chromosomal DNA from *Corynebacterium glutamicum* ATCC 13032 was isolated as described by Tauch et al. (1995, Plasmid 33:168–179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Molecular Biochemicals, Mannheim, Germany, Product Description SAP, Code no. 1758250). The DNA of the cosmid vector SuperCos1 (Wahl et al. (1987) Proceedings of the National Academy of Sciences USA 84:2160–2164), obtained from the company Stratagene (La Jolla, USA, Product Description SuperCos1 Cosmid Vektor Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase. The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC13032 DNA gemischt and the batch was treated with T4 DNA ligase (Amersham Pharmacia, Freiburg, Germany, Product Description T4-DNA-Ligase, Code no.27-0870-04). The ligation mixture was then packed in phages with the aid of Gigapack II XL Packing Extracts (Stratagene, La Jolla, USA, Product Description Gigapack II XL Packing Extract, Code no. 200217). For infection of the *E. coli* strain NM554 (Raleigh et al. 1988, Nucleic Acid Research 16:1563–1575) the cells were taken up in 10 mM $MgSO_4$ and mixed with an aliquot of the phage suspension. The infection and titering of the cosmid library were carried out as described by Sambrook et al. (1989, Molecular Cloning: A laboratory Manual, Cold Spring Harbor), the cells being plated out on LB agar (Lennox, 1955, Virology, 1:190) with 100 µg/ml ampicillin. After incubation overnight at 37° C., recombinant individual clones were selected.

Example 2

Isolation and Sequencing of the dapF Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany). The DNA of the sequencing vector pZero-1, obtained from the company Invitrogen (Groningen, The Netherlands, Product Description Zero Background Cloning Kit, Product No. K2500-01)

were cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol Letters, 123:343–7) into the E. coli strain DH5αMCR (Grant, 1990, Proceedings of the National Academy of Sciences U.S.A., 87:4645–4649) and plated out on LB agar (Lennox, 1955, Virology, 1:190) with 50 µg/ml zeocin. The plasmid preparation of the recombinant clones was carried out with Biorobot 9600 (Product No. 900200, Qiagen, Hilden, Germany). The sequencing was carried out by the dideoxy chain-stopping method of Sanger et al. (1977, Proceedings of the National Academy of Sciences U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231) version 97-0. The individual sequences of the pZero1 derivatives were assembled to a continuous contig. The computer-assisted coding region analyses were prepared with the XNIP program (Staden, 1986, Nucleic Acids Research, 14:217–231). Homology analyses were carried out with the "BLAST search programs" (Altschul et al., 1997, Nucleic Acids Research, 25:3389–3402), against the non-redundant databank of the "National Center for Biotechnology Information" (NCBI, Bethesda, MD, USA).

The nucleotide sequence obtained is shown in SEQ ID NO 1. Analysis of the nucleotide sequence showed an open reading frame of 831 base pairs, which was called the dapF gene. The dapF gene codes for a polypeptide of 277 amino acids.

Example 3
Construction of the Expression Vector pEC-XT99A

The E. coli expression vector pTRC99A (Amann et al. 1988, Gene 69:301–315) was used as the starting vector for construction of the E. coli-C. glutamicum shuttle expression vector pEC-XT99A. After BspHI-restriction cleavage (Roche Diagnostics GmbH, Mannheim, Germany, Product Description BspHI, Product No. 1467123) and subsequent Klenow treatment (Amersham Pharmacia Biotech, Freiburg, Germany, Product Description Klenow Fragment of DNA Polymerase I, Product No. 27-0928-01; method of Sambrook et al., 1989, Molecular Cloning: A laboratory Manual, Cold Spring Harbor) the ampicillin resistance gene (bla) was replaced by the tetracycline resistance gene of the C. glutamicum plasmid pAG1 (GenBank Accession No. AF121000). For this, the region carrying the resistance gene was cloned as an AluI fragment (Amersham Pharmacia Biotech, Freiburg, Germany, Product Description AluI, Product No. 27-0884-01) into the linearized E. coli expression vector pTRC99A. The ligation was carried out as described by Sambrook et al. (1989, Molecular Cloning: A laboratory Manual, Cold Spring Harbor), the DNA mixture being incubated overnight with T4 ligase (Amersham Pharmacia Biotech, Freiburg, Germany, Product Description T4-DNA-Ligase, Product No. 27-0870-04). This ligation mixture was then electroporated (Tauch et al. 1994, FEMS Microbiology Letters, 123:343–7) into the E. coli strain DH5amcr (Grant, 1990, Proceedings of the National Academy of Sciences U.S.A., 87:4645–4649). The E. coli expression vector constructed was called pXT99A. The plasmid pGA1 (Sonnen et al. 1991, Gene, 107:69–74) was used as the basis for cloning a minimal replicon from Corynebacterium glutamicum. By BalI/PstI restriction cleavage (Promega GmbH, Mannheim, Germany, Product Description BalI, Product No. R6691; Amersham Pharmacia Biotech, Freiburg, Germany Product Description PstI, Product No. 27-0976-01) of the vector pGA1, it was possible to clone a fragment of 3484 bp in the vector pK18mob2 (Tauch et al., 1998, Archives of Microbiology 169:303–312) fragmented with SmaI and PstI (Amersham Pharmacia Biotech, Freiburg, Germany, Product Description SmaI, Product No. 27-0942-02, Product Description PstI, Product No. 27-0976-01). By means of BamHI/XhoI restriction cleavage (Amersham Pharmacia Biotech, Freiburg, Germany, Product Description BamHI, Product No. 27-086803, Product Description XhoI, Product No. 27-0950-01) and subsequent Klenow treatment (Amersham Pharmacia Biotech, Freiburg, Germany, Product Description Klenow Fragment of DNA Polymerase I, Product No. 27-0928-01; method of Sambrook et al., 1989, Molecular Cloning: A laboratory Manual, Cold Spring Harbor), a fragment 839 bp in size was deleted. From the construction religated with T4 ligase (Amersham Pharmacia Biotech, Freiburg, Germany, Product Description T4-DNA-Ligase, Product No. 27-0870-04), it was possible to clone the C. glutamicum minimal replicon as a fragment of 2645 bp in the E. coli expression vector pXT99A. For this, the DNA of the construction carrying the minimal replicon was cleaved with the restriction enzymes KpnI (Amersham Pharmacia Biotech, Freiburg, Germany, Product Description KpnI, Product No. 27-0908-01) and PstI (Amersham Pharmacia Biotech, Freiburg, Germany, Product Description PstI, Product No. 27-0886-03) and a 3'–5' exonuclease treatment (Sambrook et al., 1989, Molecular Cloning: A laboratory Manual, Cold Spring Harbor) was subsequently carried out by means of Klenow-Polymerase (Amersham Pharmacia Biotech, Freiburg, Germany, Product Description Klenow Fragment of DNA Polymerase I, Product No. 27-0928-01). In a parallel batch, the E. coli expression vector pXT99A was cleaved with the restriction enzyme RsrII (Roche Diagnostics, Mannheim, Germany, Product Description RsrII, Product No. 1292587) and prepared for ligation with Klenow polymerase (Amersham Pharmacia Biotech, Freiburg, Germany, Klenow Fragment of DNA Polymerase I, Product No. 27-0928-01). The ligation of the minimal replicon with the vector construction pXT99A was carried out as described by Sambrook et al. (1989, Molecular Cloning: A laboratory Manual, Cold Spring Harbor), the DNA mixture being incubated overnight with T4 ligase (Amersham Pharmacia Biotech, Freiburg, Germany, Product Description T4-DNA-Ligase, Product No. 27-0870-04). The E. coli-C. glutamicum shuttle expression vector pEC-XT99A constructed in this way was transferred into C. glutamicum by means of electroporation (Liebl et al., 1989, FEMS Microbiology Letters, 53:299–303). The transformant could be verified by analysis of the reisolated plasmid DNA. The plasmid construction thus obtained was called pEC-XT99A (FIG. 2). The E. coli strain obtained by transformation of the plasmid pEC-XT99A in the E. coli strain DH5αmcr was called DH5αmcr/pEC-XT99A.

Example 4
Expression of the dapF Gene

Starting from the nucleotide sequence of the diaminopimelate epimerase gene dapF from *C. glutamicum* ATCC 13032 shown in SEQ ID NO 1, PCR primers were synthesized (ARK Scientific GmbH Biosystems, Darmstadt, Germany). These primers were chosen so that the amplified fragment contains the gene and native ribosome binding sites thereof, but not possible promoter regions. In addition, suitable restriction cleavage sites which allow cloning into the target vector were inserted. The sequences of the PCR primers, the cleavage sites inserted (sequence underlined) and the amplified gene (the fragment size in bp is stated in parentheses) are listed in table 1.

```
Primer Sequence with restriction cleavage site               Product
dapex1 5'-ATCGTCAATTGCACCGCACAAGCCTTGGAGA-3'(SEQ ID NO:3)    dapFex
       MunI                                                  (966 bp)
dapex2 5'-GACGATGGATCCTAACGGACGAGCGCGCACTA-3'(SEQ ID NO:4)
       BamHI
```

The diaminopimelate epimerase gene dapF from *C. glutamicum* ATCC13032 was amplified using the polymerase chain reaction (PCR) and the synthetic oligonucleotides described in table 1. The PCR experiments were carried out with the Pfu DNA polymerase from the company Stratagene (La,Jolla, Calif., Product Description native Pfu DNA Polymerase, Product No. 600250) in a "PCT-100 Thermocycler" (MJ Research Inc., Watertown, Mass., USA). A single denaturing step of 3 minutes at 94° C. was followed by a denaturing step of 30 seconds at 94° C., an annealing step for 30 seconds at a primer-dependent temperature of T=(2AT+4GC) −5 ° C. (Suggs, et al., 1981, p. 683–693, In: D. D. Brown, and C. F. Fox (Eds.), Developmental biology using purified genes. Academic Press, New York, USA) and an extension step at 72° C. lasting 90 seconds. The last three steps were repeated as a cycle 30 times and the reaction was ended with an extension step of 5 minutes at 72° C. The product prepared in this manner was tested for its size by electrophoresis in agarose gel.

The *E. coli*-*C. glutamicum* shuttle expression vector pEC-XT99A shown in FIG. 1 (example 3) was used as the base vector for the expression. The resulting PCR product was cleaved completely with the restriction enzymes BamHI and MunI and ligated into the expression vector pEC-XT99A, which had also been cleaved with the enzymes EcoRI and BamHI (Amersham Pharmacia Biotech, Freiburg, Germany, Product Description EcoRI, Product No. 27-0854-03, (sic) Product Description BamHI, Product No. 27-0868-03).

In this way, the promoter-less dapF gene is brought under the control of the trc promoter contained on this plasmid.

The ligation of the dapFex amplification into the expression vector pEC-XT99A was carried out as described by Sambrook et al. (1989, Molecular Cloning: A laboratory Manual, Cold Spring Harbor), the DNA mixture being incubated overnight with T4 ligase (Amersham Pharmacia Biotech, Freiburg, Germany, Product Description T4-DNA-Ligase, Product No. 27-0870-04). This ligation mixture was then electroporated (Tauch et al. 1994, FEMS Microbiology Letters, 123:343–7) into the *E. coli* strain DH5αmcr (Grant, 1990, Proceedings of the National Academy of Sciences U.S.A., 87:4645–4649) and plated out on LB agar (Lennox, 1955, Virology, 1:190) with 5 μg/ml tetracycline and 40 μg/ml X-Gal (5-bromo-4-chloro-3-indolyl β-D-galactoside).

After incubation for 24 hours at 37° C., colonies with insert-carrying plasmids could be identified with the aid of α-complementation (Sambrook et al., 1989, Molecular Cloning: A laboratory Manual, Cold Spring Harbor). By re-isolation of the plasmid DNA by the "Alkaline lysis method" of Birnboim and Doly (1997, Nucleic Acids Research, 7: 1513–1523), the DNA of the corresponding expression construction was obtained from the transformants. Correct cloning of the expression plasmid was checked by sequencing of the insert.

The plasmid construction thus obtained was called pEC-XT99A-dapF. The *E. coli* strain obtained by transformation of the plasmid pEC-XT99A-dapF in the *E. coli* strain DH5αmcr was called DH5αMCR/pEC-XT99A-dapF.

Example 5
Transformation of the Strain DSM5715 with the Plasmids pEC-XT99A and pEC-XT99A-dapF The plasmids pEC-XT99A (example 3) and pEC-XT99A-dapF (example 4) were transformed into the strain DSM5715 by the electroporation method (Liebl et a., 1989, FEMS Microbiology Letters, 53:299–303).

The transformants obtained with the aid of the electroporation were isolated on selection agar (LBHIS agar (18.5 g/l brain-heart infusion broth, 0.5 M sorbitol, 5 g/l Bacto-tryptone, 2.5 g/l Bacto-yeast extract, 5 g/l NaCl, 18 g/l Bacto-agar)) with 15 mg/l kanamycin. Plasmid DNA was isolated by conventional methods (Peters-Wendisch et al., 1998, Microbiology, 144, 915–927), cut with suitable restriction endonucleases (PstI (Amersham Pharmacia Biotech, Freiburg, Germany, Product Description PstI, Product No. 27-0886-03))and checked. The strains obtained were called DSM5715/pEC-XT99A and DSM5715/pEC-XT99A-dapF.

Example 6
Preparation of L-lysine

The *C. glutamicum* strains DSM5715/pEC-XT99A and DSM5715/pEC-XT99A-dapF prepared in example 5 were cultured in a nutrient medium suitable for the production of lysine and the lysine content was determined in the culture supernatant.

For this, the strains were first incubated on agar plates (brain-heart agar with kanamycin (25 mg/l )) for 24 hours at 33° C. Starting from these agar plate cultures, a preculture was seeded (10 ml medium in 100 ml conical flask). The medium used for the preculture was the complete medium CgIII (Bacto-peptone 10 g/l, Bacto-yeast extract 10 g/l, NaCl 5g/l, pH 7.4 (Eggeling et al., 1987, Applied Microbiology and Biotechnology, 25:346–351). Tetracycline (5 mg/l) was added. The preculture was incubated for 24 hours at 33° C. at 240 rpm on a shaking machine. A main culture was seeded from this preculture such that the initial OD (measurement wavelength 660 nm) of the main culture was 0.2 OD. Medium MM was used for the main culture.

Medium MM:

| | |
|---|---|
| CSL | 5 g/l |
| MOPS | 20 g/l |
| Glucose | 50 g/l (autoclave separately) |
| Salts: | |
| (NH4)2SO4) [sic] | 25 g/l |
| KH2PO4 | 0.1 g/l |
| MgSO4*7H2O | 1.0 g/l |

-continued

| | |
|---|---|
| CaCl2*2H2O | 10 mg/l |
| FeSO4*7H2O | 10 mg/l |
| MnSO4*H2O | 5.0 mg/l |
| L-Leucine | 0.1 g/l |
| Biotin | 0.3 mg/l (sterile-filtered) |
| Thiamine*HCl | 0.2 mg/l (sterile-filtered) |
| CaCO3 | 25 g/l |

Abbreviations:
CSL: Corn steep liquor
MOPS: Morpholinopropanesulfonic acid

The CSL, MOPS and the salt solution are brought to pH 7 with aqueous ammonia and autoclaved. The sterile substrate and vitamin solutions are then added, and the CaCO3 autoclaved in the dry state is added.

Culturing was carried out in a 10 ml volume in a 100 ml conical flask with baffles. Tetracycline (5 mg/l) was added. Culturing was carried out at 33° C. and 80% atmospheric humidity.

To induce the dapF expression, 1 mM IPTG (isopropyl thio-β-galactoside, Gibco BRL Life Technologies, Eggenstein, Germany) Catalogue Number 15529-019) was added.

After 72 hours, the OD at a measurement wavelength of 660 nm and the concentration of lysine formed were determined. An LD 1W digital photometer from the company (Lange, Berlin, Germany) was employed for determination of the optical density (OD660). Lysine was determined with an amino acid analyzer from the company Eppendorf-BioTronik (Hamburg, Germany) by ion exchange chromatography and post-column derivatization with ninhydrin detection.

The result of the experiment is shown in table 2.

TABLE 2

| Strain | IPTG | OD | L-Lysine g/l |
|---|---|---|---|
| DSM5715/pEC-XT99A | | 8.2 | 11.9 |
| DSM5715/pEC-XT99A-dapF | | 8.5 | 12.6 |
| DSM5715/pEC-XT99A-dapF | 1 mM | 9.1 | 13.5 |

Figure 1:
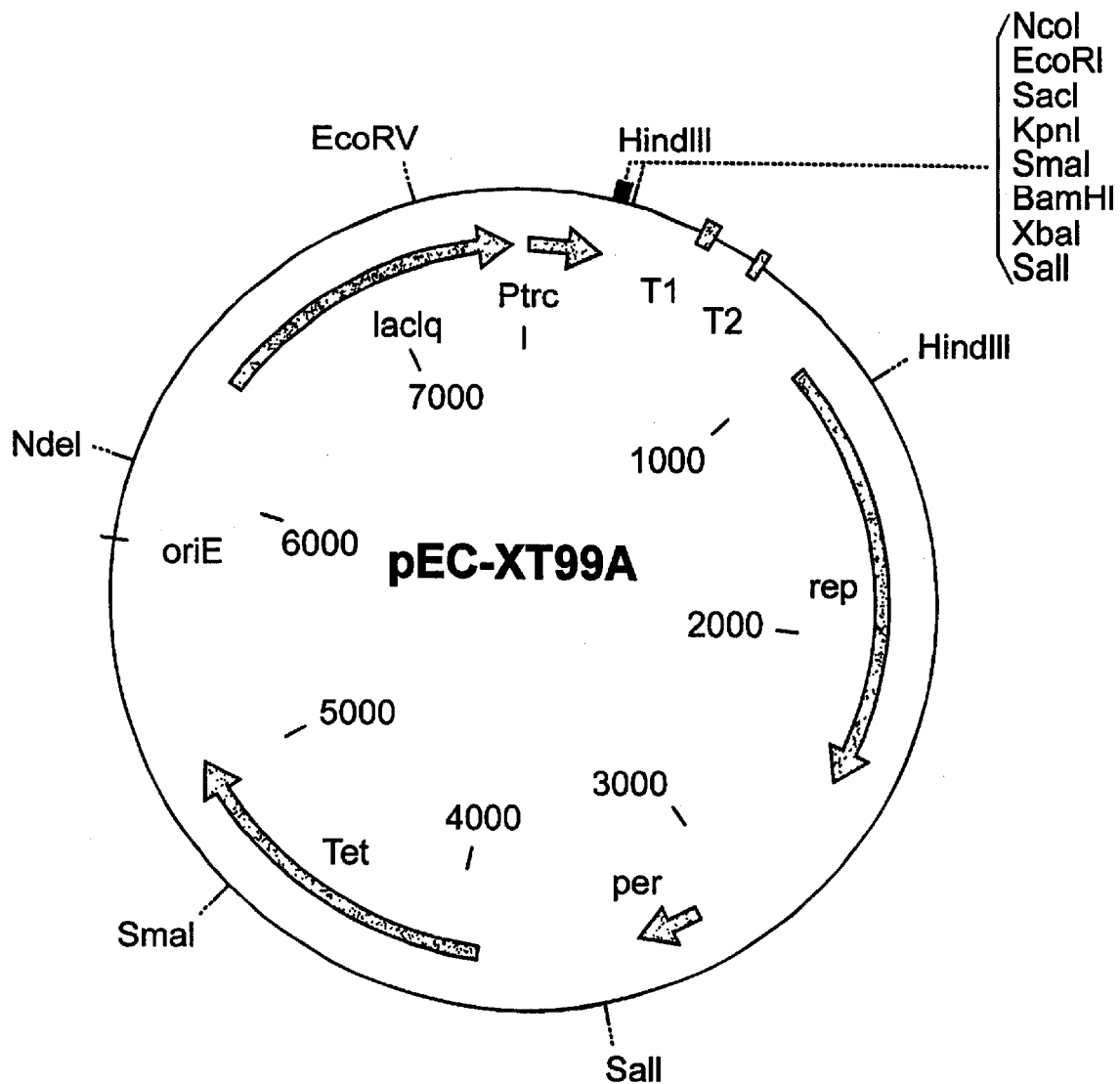
FIG. 1: Map of the plasmid pEC-XT99A.
Figure 2:
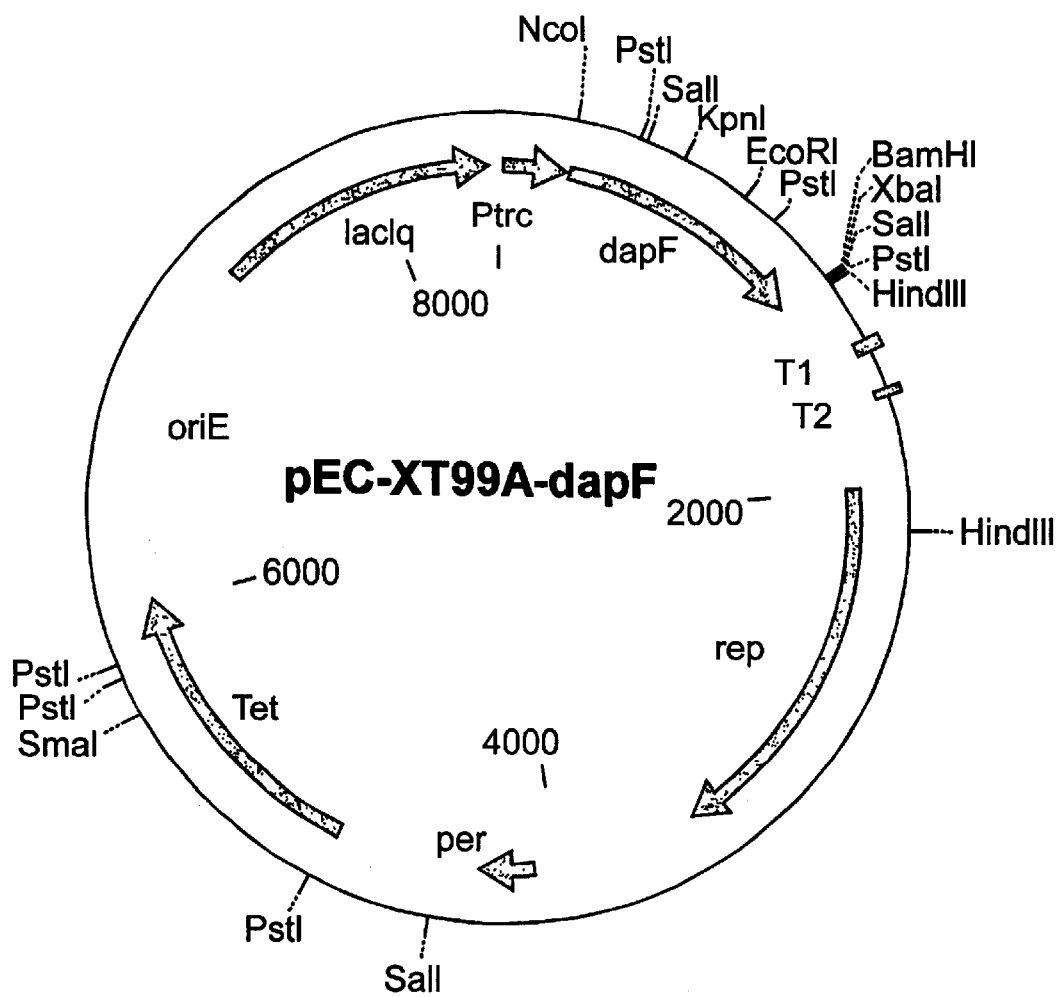
FIG. 2: Map of the plasmid pEC-XT99AdapF

The abbreviations used in the figures have the following meaning:

Tet: Resistance gene for tetracycline
dapF: dapF gene of *C. glutamicum*
oriE: Plasmid-coded replication origin from *E. coli*
rep: Plasmid-coded replication origin from *C. glutamicum* plasmid pGA1
per: Gene for controlling the number of copies from PGA1
EcoRI: Cleavage site of the restriction enzyme EcoRI
EcoRV: Cleavage site of the restriction enzyme EcoRV
HincII: Cleavage site of the restriction enzyme HincII
HindIII: Cleavage site of the restriction enzyme HindIII
KpnI: Cleavage site of the restriction enzyme KpnI
SalI: Cleavage site of the restriction enzyme SalI
SmaI: Cleavage site of the restriction enzyme SmaI
SphI: Cleavage site of the restriction enzyme SphI
PvuII: Cleavage site of the restriction enzyme PvuII
BamHI: Cleavage site of the restriction enzyme BamHI

What is claimed is:

1. An isolated polynucleotide comprising a nucleotide sequence that encodes SEQ ID NO:2.

2. The isolated polynucleotide of claim 1, wherein the nucleotide sequence is identical to SEQ ID NO:1 from nucleotides 151–981.

3. The isolated polynucleotide of claim 1, wherein the nucleotide sequence is SEQ ID NO:1.

4. An isolated polynucleotide consisting of SEQ ID NO:1.

5. An isolated polynucleotide consisting of SEQ ID NO:1 from nucleotides 151–981.

6. A vector comprising the polynucleotide of any one of claims 1, 2, and 3.

7. A host cell comprising the vector of claim 6.

8. A vector for expression of dapF from *C. glutamicum* comprising a promoter operably linked to a coding sequence, wherein said coding sequence comprises the polynucleotide of any one of claims 1, 2, and 3.

9. A bacterial cell transformed with the vector of claim 8.

10. A process for the production of L-lysine comprising:
 a) culturing the bacterial cell of claim 9 under conditions suitable for the expression of the coding sequence; and
 b) recovering L-lysine from the bacterial culture, wherein said bacteria produce L-lysine.

11. The process of claim 10, wherein said bacterial cell also overexpresses one or more genes encoding the following:
 dihydrodipicolinate synthase,
 the protein which imparts S-(2-amino ethyl)-cysteine resistance,
 tetradihydro-dipicolinate succinylase, and
 succinyldiaminopimelate desuccinylase;
 wherein said genes are native to *C. glutamicum*.

12. The process of claim 10, wherein said bacterial cell also overexpresses the gene encoding the protein which imparts S-(2-amino ethyl)-cysteine resistance, wherein said gene is native to *C. glutamicum*.

* * * * *